(12) United States Patent
Schabron

(10) Patent No.: US 8,525,114 B2
(45) Date of Patent: Sep. 3, 2013

(54) STANDOFF EXPLOSIVES DETECTION

(75) Inventor: John F. Schabron, Laramie, WY (US)

(73) Assignee: University of Wyoming Research Corporation, Laramie, WY (US)

( * ) Notice: Subject to any disclaimer, the term of this patent is extended or adjusted under 35 U.S.C. 154(b) by 1306 days.

(21) Appl. No.: 11/985,275

(22) Filed: Nov. 13, 2007

(65) Prior Publication Data

US 2012/0241621 A1 Sep. 27, 2012

Related U.S. Application Data

(60) Provisional application No. 60/859,282, filed on Nov. 14, 2006.

(51) Int. Cl.
*G01J 3/427* (2006.01)

(52) U.S. Cl.
USPC .............. 250/339.12; 250/339.11; 250/338.1; 250/341.8; 250/339.1

(58) Field of Classification Search
USPC ................. 250/339.11, 339.12, 338.1, 341.8, 250/339.1
See application file for complete search history.

(56) References Cited

U.S. PATENT DOCUMENTS

| | | | |
|---|---|---|---|
| 4,840,706 A * | 6/1989 | Campbell | 162/198 |
| 4,866,439 A | 9/1989 | Kraus | |
| 5,135,704 A | 8/1992 | Shefer et al. | |
| 5,138,889 A | 8/1992 | Conrad | |
| 5,255,556 A | 10/1993 | Lobdell | |
| 5,278,418 A | 1/1994 | Broadhurst | |
| 5,345,809 A | 9/1994 | Corrigan et al. | |
| 5,585,575 A | 12/1996 | Corrigan et al. | |
| 5,648,047 A | 7/1997 | Kardish et al. | |
| 5,680,470 A | 10/1997 | Moussa et al. | |
| 5,854,431 A | 12/1998 | Linker et al. | |
| 5,942,699 A | 8/1999 | Ornath et al. | |
| 5,956,409 A | 9/1999 | Chan et al. | |
| 6,047,588 A | 4/2000 | Danilychev | |
| 6,085,601 A | 7/2000 | Linker et al. | |
| 6,192,766 B1 | 2/2001 | Gardhagen et al. | |
| 6,406,918 B1 | 6/2002 | Bannister et al. | |
| 6,477,905 B1 | 11/2002 | Mitra | |
| 6,518,584 B1 * | 2/2003 | Woodruff | 250/504 H |
| 6,773,674 B2 | 8/2004 | Bannister et al. | |

(Continued)

FOREIGN PATENT DOCUMENTS

GB 2297377 A 7/1996
WO WO 2007/100761 A2 9/2007

OTHER PUBLICATIONS

Existing and Potential Standoff Explosives Detection Techniques; Committee on the Review of Existing and Potential Standoff Explosives Detection Techniques, Board on Chemical Sciences and Technology, Division on Earth and Life Studies, 5 pages, 2004.

(Continued)

*Primary Examiner* — David Porta
*Assistant Examiner* — Djura Malevic
(74) *Attorney, Agent, or Firm* — Santangelo Law Offices, P.C.

(57) ABSTRACT

The present invention may include methods and apparatus for the detection of explosives using near infrared or infrared spectroscopy to detect nitro or even carbonyl groups. Embodiments may include, at least one radiation emitter may emit at least one wavelength towards a target. At least one reflected wavelength may be generated after the wavelength collides with the target. A reflected wavelength may then be detected by at least one detector and analyzed with an analyzer.

25 Claims, 16 Drawing Sheets

(56) References Cited

U.S. PATENT DOCUMENTS

| | | |
|---|---|---|
| 6,794,645 B2 | 9/2004 | Kanik et al. |
| 6,861,646 B2 | 3/2005 | Motchkine et al. |
| 6,870,155 B2 | 3/2005 | Krasnobaev et al. |
| 6,888,128 B2 | 5/2005 | Krasnobaev et al. |
| 6,895,804 B2 | 5/2005 | Lovell et al. |
| 6,922,460 B2 | 7/2005 | Skatter et al. |
| RE38,797 E | 9/2005 | Linker et al. |
| 6,952,163 B2 | 10/2005 | Huey et al. |
| 7,098,672 B2 | 8/2006 | Belyakov et al. |
| 7,840,360 B1 * | 11/2010 | Micheels et al. .............. 702/25 |
| 2003/0116705 A1 | 6/2003 | Kanik et al. |
| 2003/0155504 A1 | 8/2003 | Motchkine et al. |
| 2003/0155506 A1 | 8/2003 | Motchkine et al. |
| 2004/0155181 A1 | 8/2004 | Krasnobaev et al. |
| 2004/0165750 A1 | 8/2004 | Chew |
| 2004/0227073 A1 | 11/2004 | Krasnobaev et al. |
| 2004/0252024 A1 | 12/2004 | Huey et al. |
| 2004/0252807 A1 | 12/2004 | Skatter et al. |
| 2005/0007119 A1 | 1/2005 | Belyakov et al. |
| 2005/0010374 A1 * | 1/2005 | Li .................................. 702/28 |
| 2005/0024199 A1 | 2/2005 | Huey et al. |
| 2005/0025280 A1 | 2/2005 | Schulte |
| 2005/0101027 A1 | 5/2005 | Haas |
| 2005/0133716 A1 | 6/2005 | Miller et al. |
| 2005/0177271 A1 | 8/2005 | Koren |
| 2005/0253080 A1 * | 11/2005 | Janik ............................. 250/372 |
| 2007/0212791 A1 | 9/2007 | Hummel et al. |
| 2007/0221863 A1 | 9/2007 | Zipf |
| 2007/0228280 A1 | 10/2007 | Mueller |
| 2010/0164718 A1 * | 7/2010 | Parish et al. .................. 340/540 |
| 2010/0278441 A1 * | 11/2010 | Shashidhar .................. 382/218 |

OTHER PUBLICATIONS

Welcome to U.S. Air Force AIM Points; Pentagon widens program to foil bombings in Iraq, Eric Schmitt, New York Times, 1 page, printed Feb. 6, 2006.

Raman Sample Spectra; http://www.oceanoptics.com/products/2001spectra.asp; 5 pages, printed Jan. 18, 2006.

TSWG Technical Support Working Group; TSWG.gov-Explosives Detection; http://www.tswg.gov/tswg/ed/ed_ma.htm; 4 pages, printed Apr. 25, 2006.

Photoluminescence spectroscopy: New technique for detecting explosives; Vishwas Purohit, 2 pages, Oct. 11, 2004; http://www.buzzle.com/editorials/10-11-2004-60363.asp printed Apr. 25, 2006.

LaSen, Inc., Airborne Pipeline Inspection Systems (ALPIS) Field Demonstration at the Rocky Mountain Oilfield Testing Center (RMOTC), Sep. 13, 2004-Sep. 17, 2004, submitted to the Department of Transportation, Office of Pipeline Safety, 6 pages.

Independent Business & Scientific Group, Light Emitting Diodes, www.ibsg-st-petersburg.com, Web pages printed Nov. 13, 2006, 11 pages.

US Provisional Application, entitled Remote Detection of Improvised Explosive Devices, filed Nov. 14, 2006; U.S. Appl. No. 60/859,282; 27 pages.

* cited by examiner

STANDOFF EXPLOSIVES DETECTION

This is a U.S. Non-Provisional Patent Application claiming the benefit of U.S. Provisional Patent Application No. 60/859,282, filed Nov. 14, 2006, hereby incorporated by reference herein.

BACKGROUND OF THE INVENTION

Improvised explosive devices ("IED") are a significant cause of fatalities for U.S. service personnel in Iraq and Afghanistan. They are also a concern in screening materials for airport security. The present invention represents various approaches to IED detection. This approach could also be applied to a device for screening liquid containers, such as water bottles at airports.

Other explosive detection devices may include: ion mobility spectrometers as discussed in U.S. Pat. No. 7,098,672 to Belyakov, hereby incorporated by reference; use of ultraviolet, visible, or infrared light to identify explosives as discussed in U.S. Pat. Pub. No. 2007/0212791 to Hummel, hereby incorporated by reference; use of near infrared spectroscopy to detect —OH, —CH, or —NH bonds as discussed in UK Pat. Pub. No. GB2297377A to Burrows, hereby incorporated by reference; use of photoluminescence for the detection of TNT as discussed in Buzzle.com (web article, "Photoluminescence spectroscopy: New technique for detecting explosives" by Vishwas Purohit of Oct. 11, 2004 at http://www.buzzle.com/editorials/10-11-2004-60363.asp), hereby incorporated by reference; use of THz-radiation for identification of concealed objects as discussed in U.S. Pat. Pub. No. 2007/0228280 to Mueller, hereby incorporated by reference; use of quadrupole resonance detection for detecting explosives as discussed in PCT Pub. No. WO2007/100761 to Schiano, hereby incorporated by reference; and use of ultraviolet light for detection of explosives as discussed in U.S. Pat. Pub. No. US2007/0221863 to Zipf, hereby incorporated by reference.

None of the past references use NIR spectroscopy to detect certain chemical groups indicative of explosive devices, namely carbonyl and nitro groups. Specifically, the Hummel reference does not mention the use of near infrared spectroscopy with the detection of explosives. Near infrared detection ("NIR") is different from infrared ("IR") detection. NIR may include wavelengths of about 800 nm to about 2500 nm and IR may include wavelengths of about 2500 nm to about 15,380 nm and they can require different equipment and sample handling techniques for each. Further, the Hummel reference describes use with Differential Reflectance Spectra, which may scan a wavelength region at two different and spaced apart locations on the sample.

Further, the Burrows reference does not mention the detection of carbonyl or even nitro groups of explosive devices. Burrows may have found that detection of —OH, —CH, or —NH groups are easily accessible by use with a tungsten-halogen lamp (e.g., a light bulb). Burrows did not look at longer wavelengths of the NIR spectrum since at that time, no-one was aware that use with longer wavelengths, e.g., use with NIR at 2200 nm, might be useful for explosive detection, namely nitro and carbonyl groups of explosives. The present invention, in embodiments, entails use with specific NIR optics to achieve a desired wavelength region in order to detect nitro and carbonyl groups.

SUMMARY OF INVENTION

The present invention may include, in embodiments, methods for detecting explosives using spectroscopy to detect chemical groups such as nitro groups or even carbonyl groups found in common explosive compounds.

As such, it is one object of the present invention, in embodiments, to provide the detection of explosives using near infrared spectroscopy.

It is another object of the present invention, in embodiments, to provide the detection of explosives using infrared spectroscopy.

It is yet another object of the present invention, in embodiments, to provide the detection of carbonyl and perhaps even nitro groups of explosives using optical techniques such as lasers and the like.

Naturally, further objects, goals and embodiments of the inventions are disclosed throughout other areas of the specification.

DETAILED DESCRIPTION OF THE PREFERRED EMBODIMENTS

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

The present invention may include, in embodiments, methods and apparatus for the detection of explosives. In an embodiment, the present invention may include a method of detecting explosives comprising the steps of directing a radiation emitter onto a target, emitting radiation having at least one near infrared wavelength from said radiation emitter towards said target, colliding said at least one near infrared wavelength with said target, generating at least one reflected near infrared wavelength after said collision of said at least one near infrared wavelength with said target, detecting an intensity of said at least one reflected near infrared wavelength, analyzing said intensity of said at least one reflected near infrared wavelength, and determining if said target has molecules of a chemical group selected from a group consisting of a nitro group and a carbonyl group based on said step of analyzing said intensity of said at least one reflected near infrared wavelength.

Another embodiment of the present invention may include an explosive detection apparatus comprising a radiation emitter, at least one near infrared wavelength generated from said radiation emitter, a reflected near infrared wavelength detector of at least one reflected near infrared wavelength generated after said at least one near infrared wavelength collides with a target, and a reflected near infrared wavelength analyzer to determine if said target has molecules of a chemical group selected from a group consisting of a nitro group and a carbonyl group.

Figure 1:
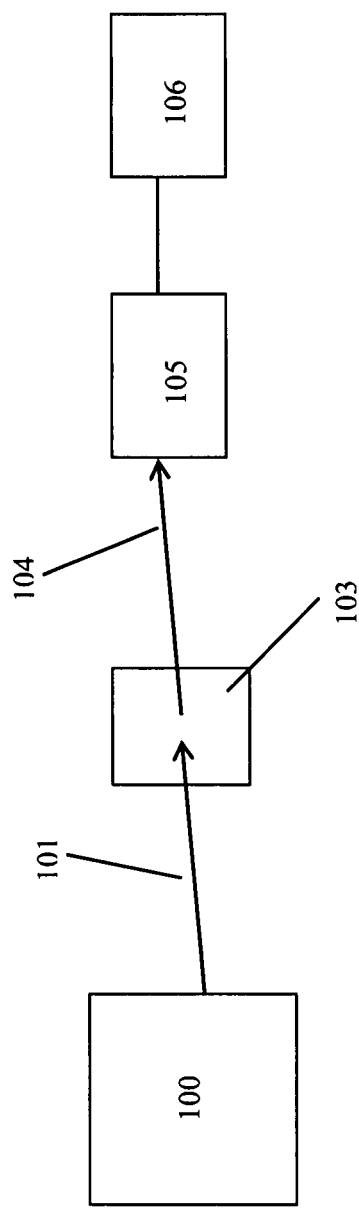
FIG. 1 represents an example of an explosive detection system having a radiation emitter, at least one wavelength, a target, a reflected wavelength, a detector and analyzer in accordance with some embodiments of the present invention.

As can be shown in FIG. 1, at least one radiation emitter (100) may emit at least one wavelength (101) towards a target (103). At least one reflected wavelength (104) may be generated after the wavelength collides with the target. A reflected wavelength may then be detected by at least one detector (105) and analyzed with an analyzer (106).

In embodiments, a wavelength (101) may include a near infrared wavelength, an infrared wavelength, wavelengths from other ranges of an electromagnetic spectrum, and the like. Embodiments of the present invention may include the use of at least one, or perhaps even at least two, near infrared wavelengths directed at a target. In those applications where more than one wavelength may be directed onto a target, at least one wavelength may be absorbed by the target and at least one other wavelength may be absorbed to a lesser extent or perhaps not absorbed at all by a target. After wavelengths may collide with a target, at least one, perhaps even at least two, reflected wavelengths (104) may be generated.

Embodiments of the present invention may be based on techniques such as Light Detection And Ranging ("LIDAR") or perhaps even Differential Absorption Lidar ("DIAL") which may include techniques for measuring chemicals by using two different laser wavelengths: one that is absorbed by the chemical of interest, and one that may be absorbed to a lesser extent or perhaps not absorbed at all. The difference in intensity or perhaps even ratio of intensity of the two beams may be used to detect the presence and/or concentration of a chemical. LIDAR imaging may be employed to profile potential targets in two or three dimensions.

Figure 10:
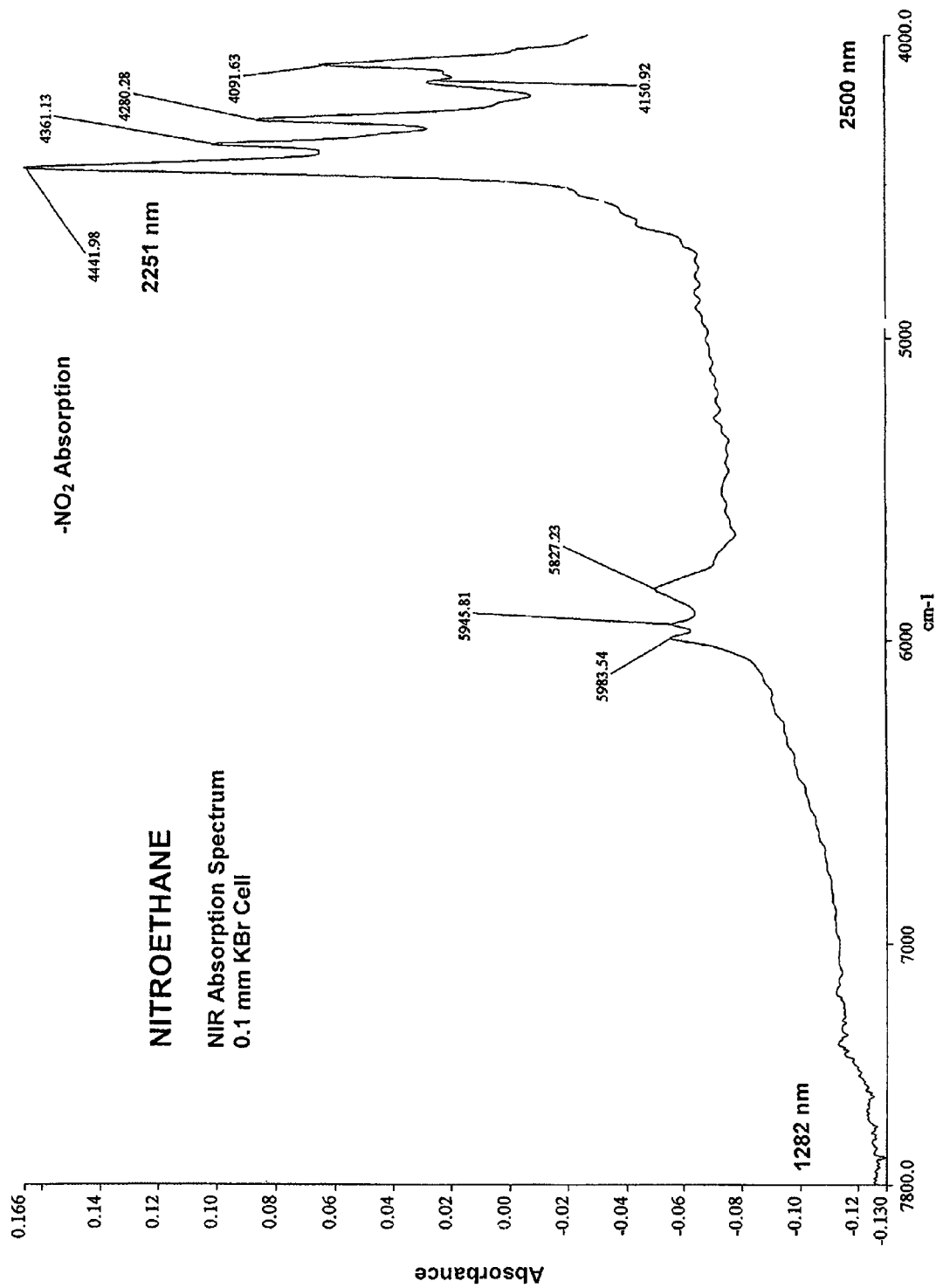
FIG. 10 shows a nitroethane NIR absorption spectrum in accordance with some embodiments of the present invention.

In some embodiments, a radiation emitter (100) may include, but it is not limited to an incandescent lamp, a laser, a near infrared laser, a solid state laser, a solid state diode laser, a continuous Mode laser, a pulsed mode laser, a boxcar integrated laser, a tunable diode laser, and the like. An IED detector system may include lasers to perform Near-Infrared ("NIR") detection of IED's perhaps based on absorption by the presence of a nitro (—$NO_2$) functional group in explosives. The NIR region may typically be defined as the region from about 12,500 $cm^{-1}$ (about 800 nm) to about 4,000 $cm^{-1}$ (about 2,500 nm). In chemicals commonly used for explosives, the nitro group may provide an on-board oxidant that may cause explosive chemicals such as trinitrotoluene, nitroglycerine, nitrocellulose, and the like to instantaneously oxidize when ignited. The —$NO_2$ group may have a strong infrared absorbance in the mid-IR region from about 1500 $cm^{-1}$ to about 1600 $cm^{-1}$ due to —N═O stretch, perhaps corresponding to a wavelength of about 6667 nm to about 6250 nm. The third harmonic wavelengths of these frequencies may occur from about 2222 nm to about 2083 nm, respectively. The actual harmonic frequencies may be due to complex peak harmonics and vibrational interactions. The absorbance due to the nitro group in this region may be shown in the NIR spectrum of nitroethane in FIG. 10.

Solid state lasers, perhaps those which may have been used in surgical procedures, are available for wavelengths of about 2100 nm (holmium:YAG) and about 2060 nm (holmium: YLF). It may be possible that by illuminating vapors from explosive chemicals containing nitro groups with both laser wavelengths in air or perhaps even on a solid surface, the presence of such chemicals may be detected. In embodiments, the nitro group may absorb light of about 2100 nm, but perhaps may not absorb light of about 2060 nm, for example, which may then be used as a reference beam. A simple ratio of scattered or perhaps even reflected light for two wavelengths, (i.e. about 2100 nm/about 2060 nm intensities) from a focused detector may possibly serve as a remote indicator of IEDs. Other lasers may be used, for example erbium:glass at 1540 nm, and the like.

Another functional group that may absorb near this region may include the carbonyl group (—C═O) which may be found in carboxylic acids, aldehydes, and ketones; however, these may absorb at frequencies of about 1600 $cm^{-1}$ or higher (perhaps less than about 2080 nm third harmonic). This could be a possible source of interference; however with careful wavelength selection and signal processing, it could be possible to distinguish these from the nitro groups in explosives. With appropriate signal processing, however the carbonyl absorption could also possibly be used to detect the presence of the non-nitro carbonyl containing explosive triacetone triperoxide ("TATP").

Figure 2:
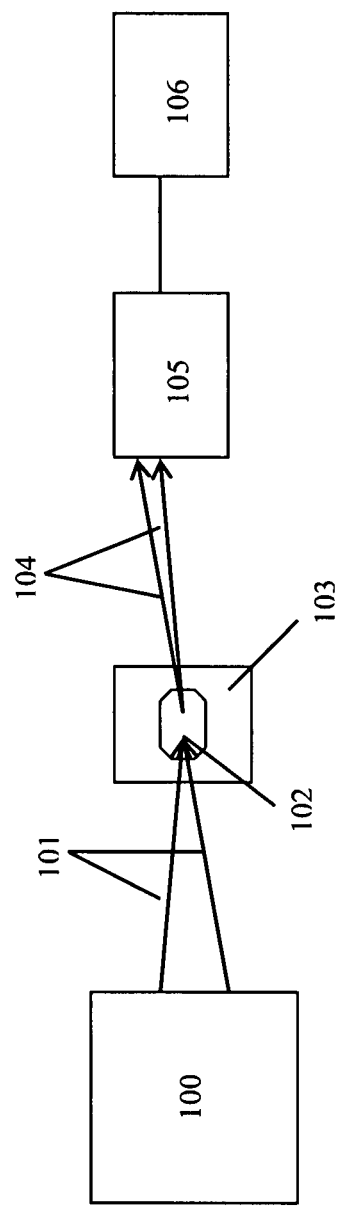
FIG. 2 represents an example of an explosive detection system having a radiation emitter, at least two wavelengths, a target, a reflected wavelength, a detector, and an analyzer in accordance with some embodiments of the present invention.
Figure 3:
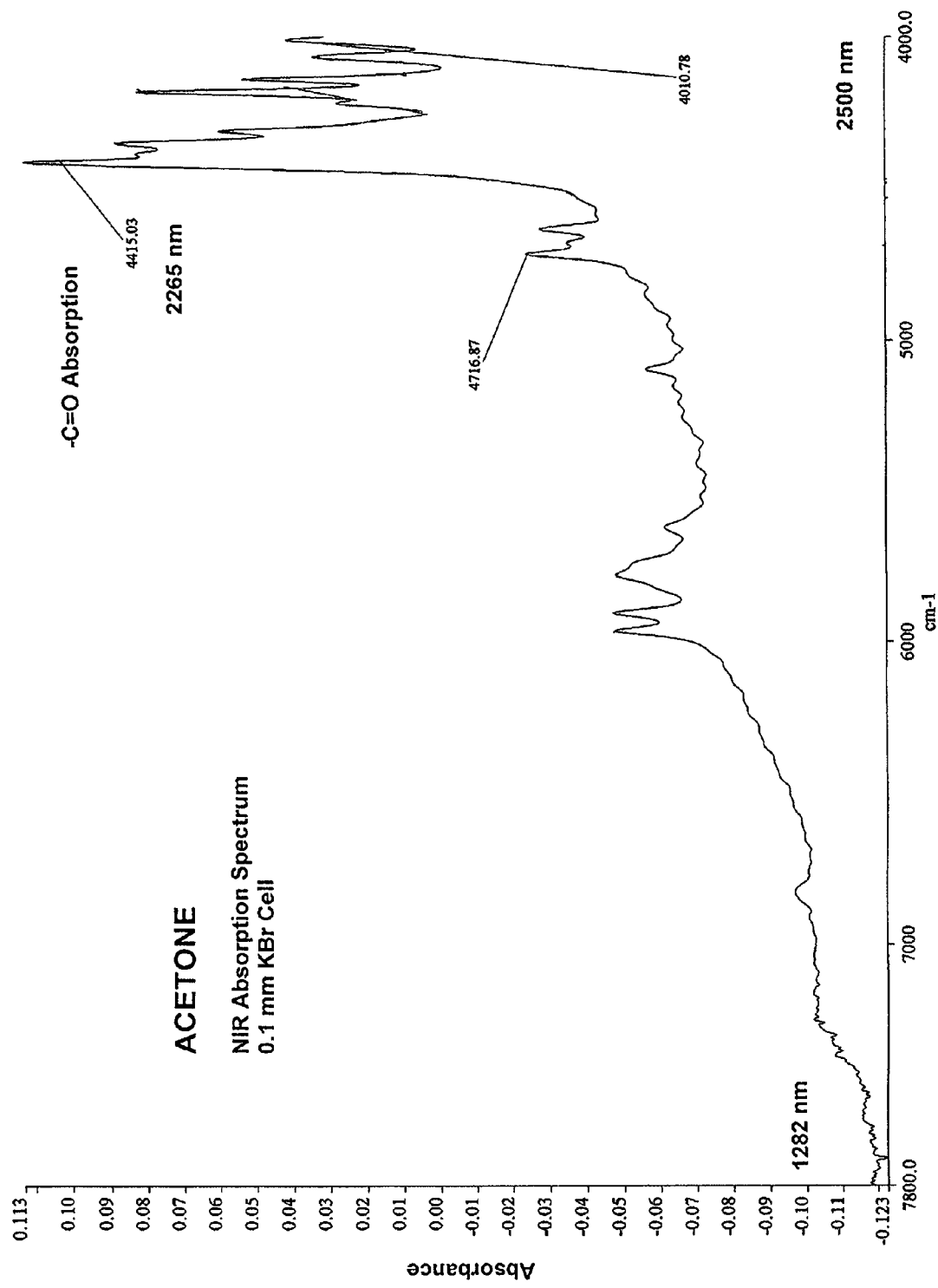
FIG. 3 shows an acetone NIR absorption spectrum in accordance with some embodiments of the present invention.
Figure 4:
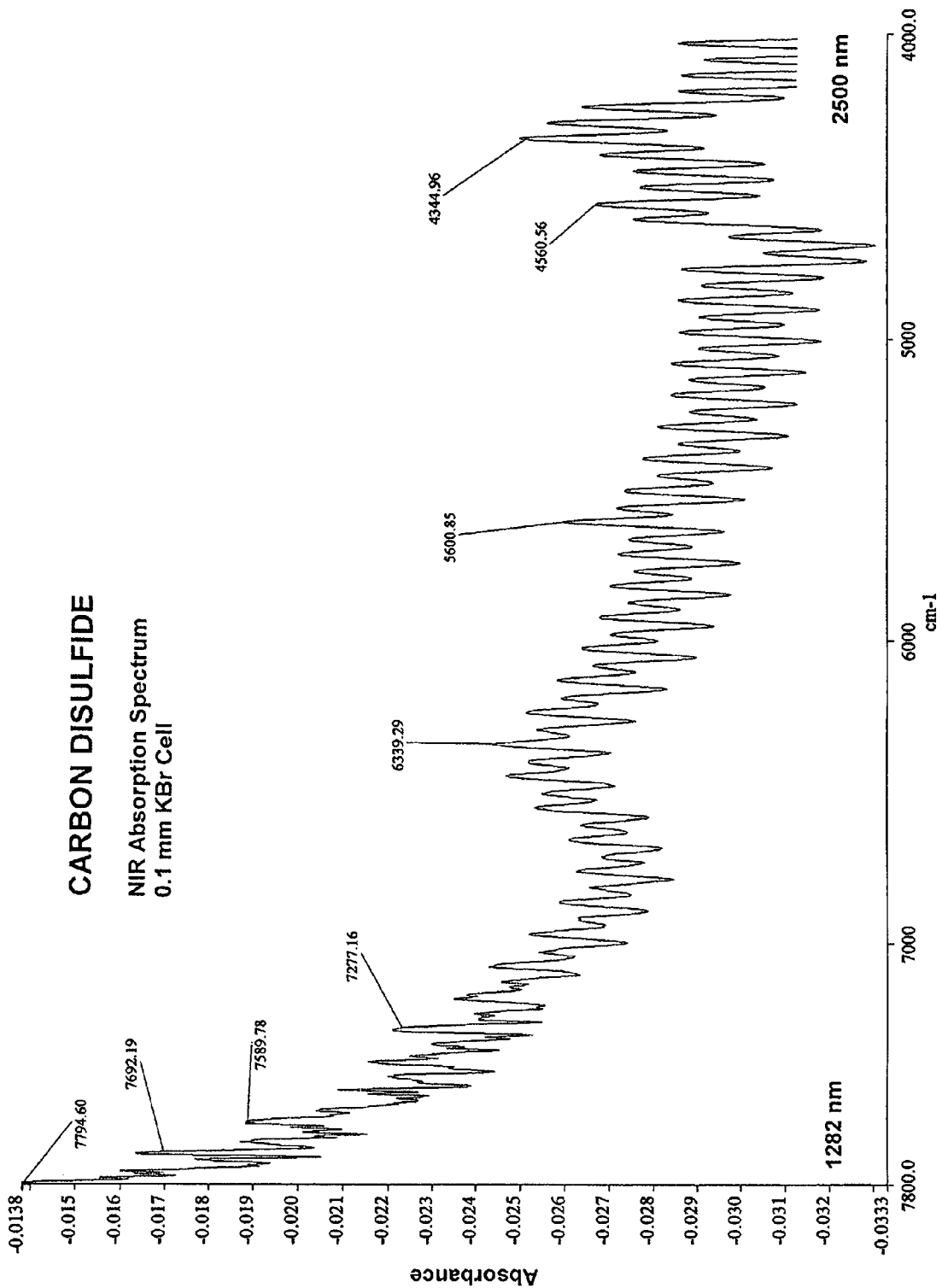
FIG. 4 shows a carbon disulfide NIR absorption spectrum in accordance with some embodiments of the present invention.
Figure 5:
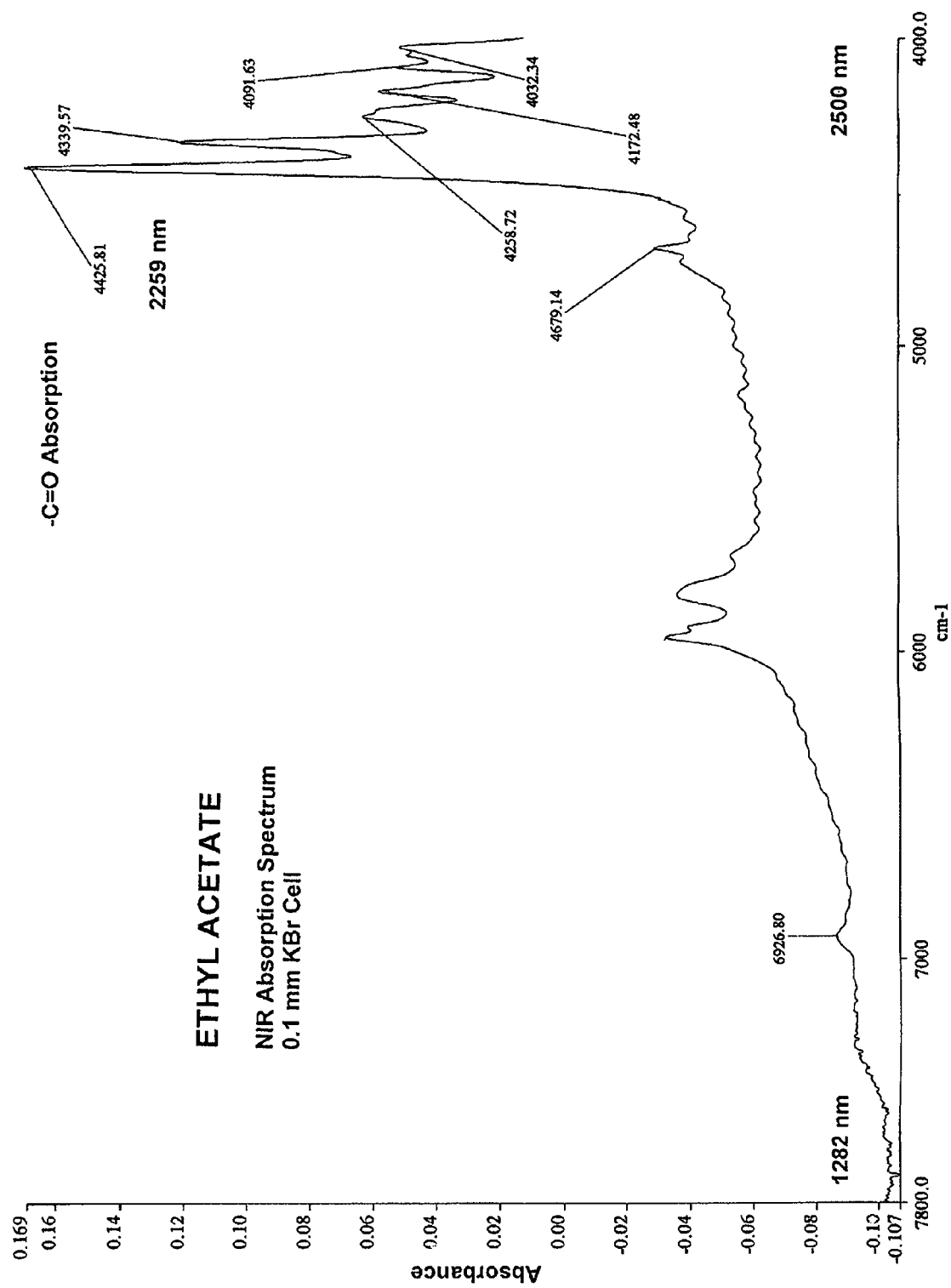
FIG. 5 shows an ethyl acetate NIR absorption spectrum in accordance with some embodiments of the present invention.
Figure 6:
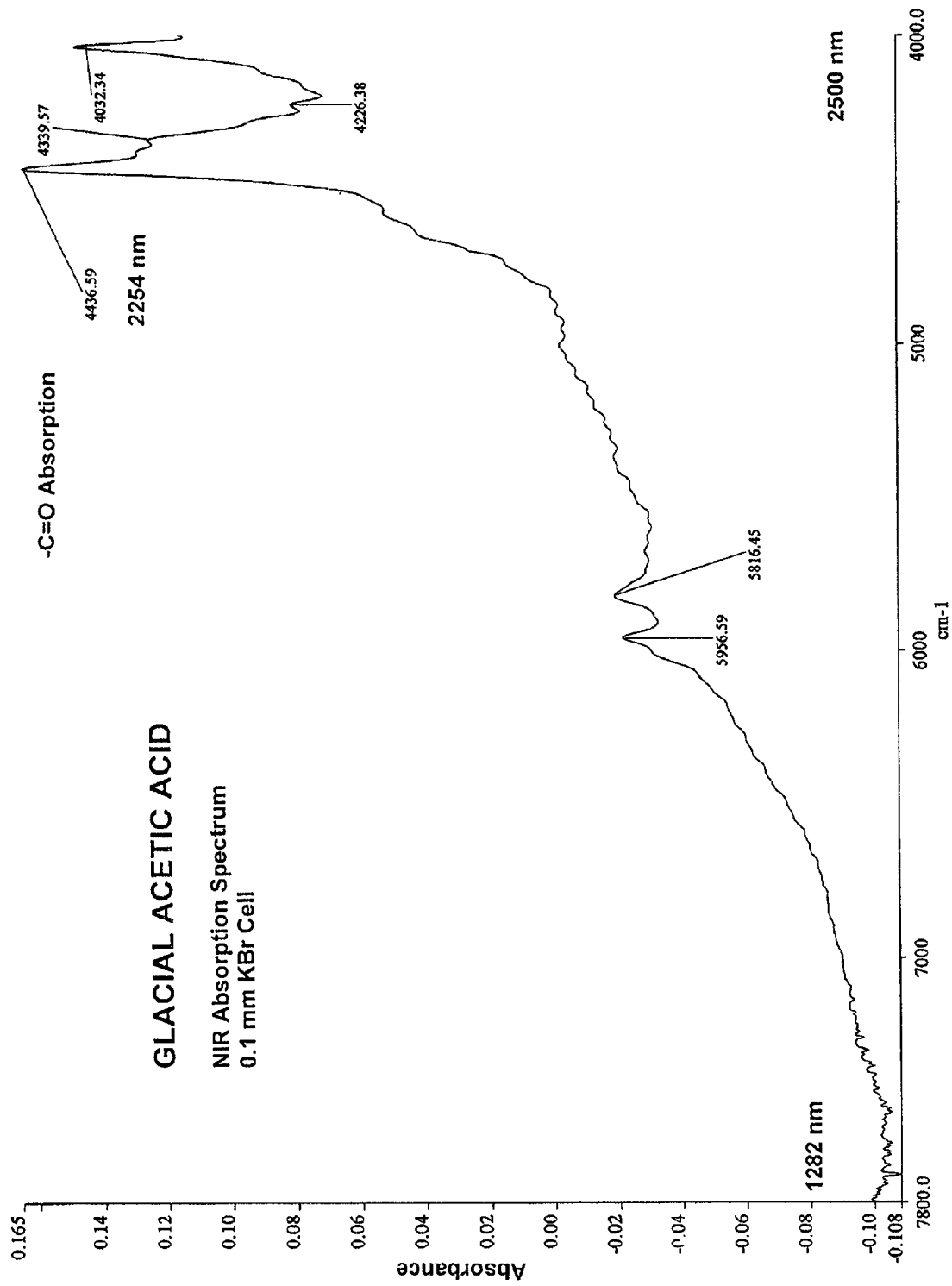
FIG. 6 shows a glacial acetic acid NIR absorption spectrum in accordance with some embodiments of the present invention.
Figure 7:
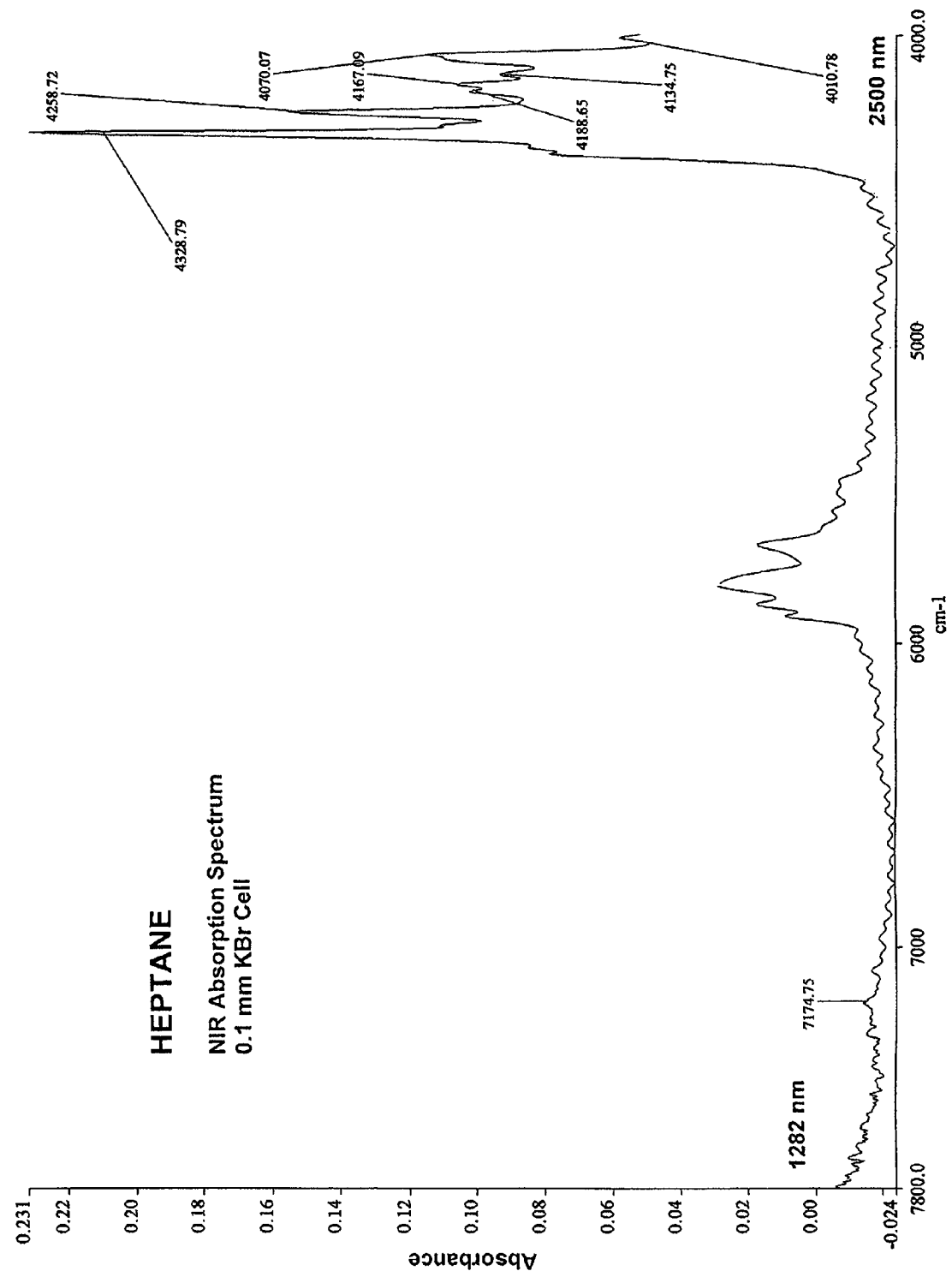
FIG. 7 shows a heptane NIR absorption spectrum in accordance with some embodiments of the present invention.
Figure 8:
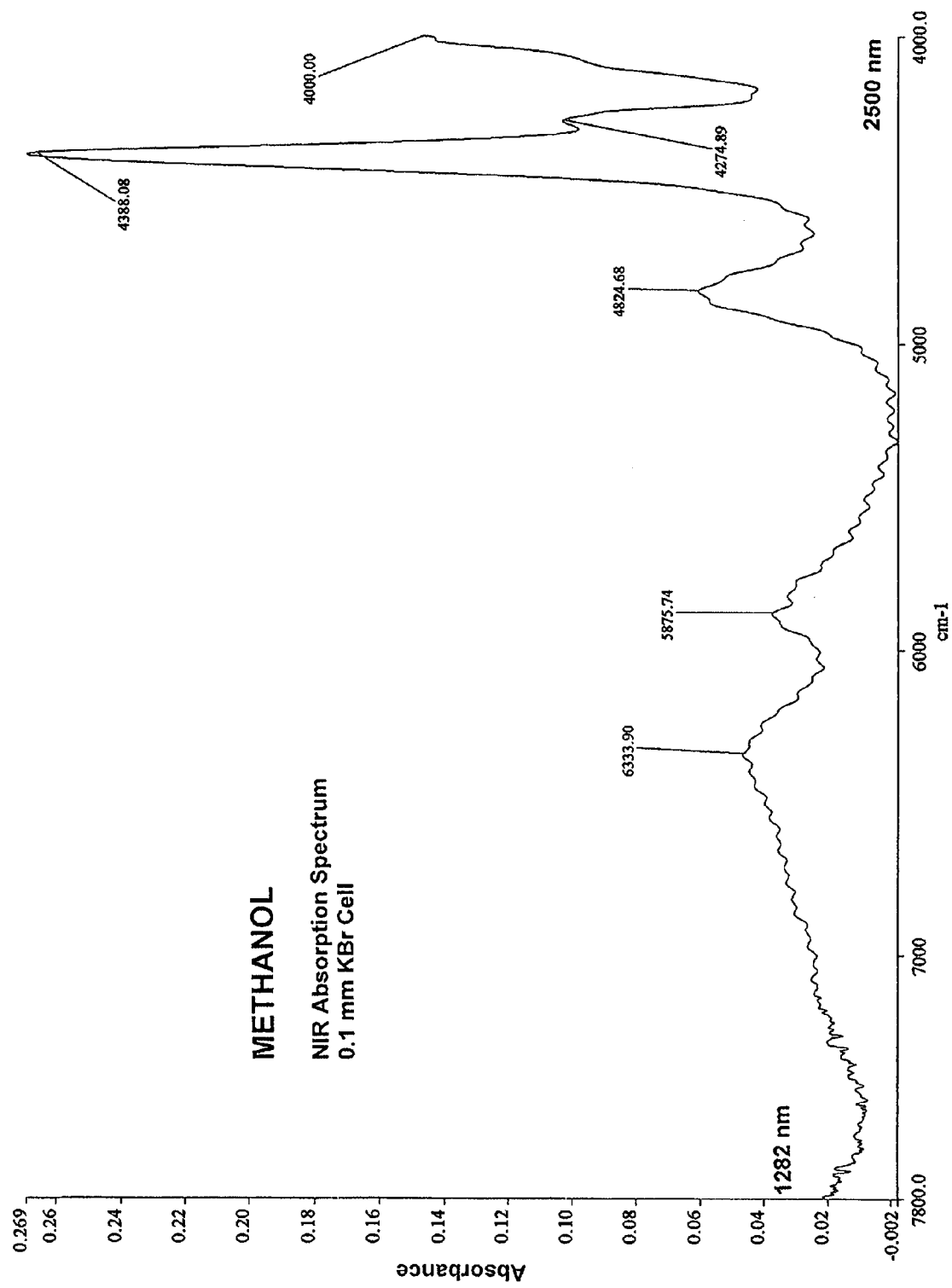
FIG. 8 shows a methanol NIR absorption spectrum in accordance with some embodiments of the present invention.
Figure 9:
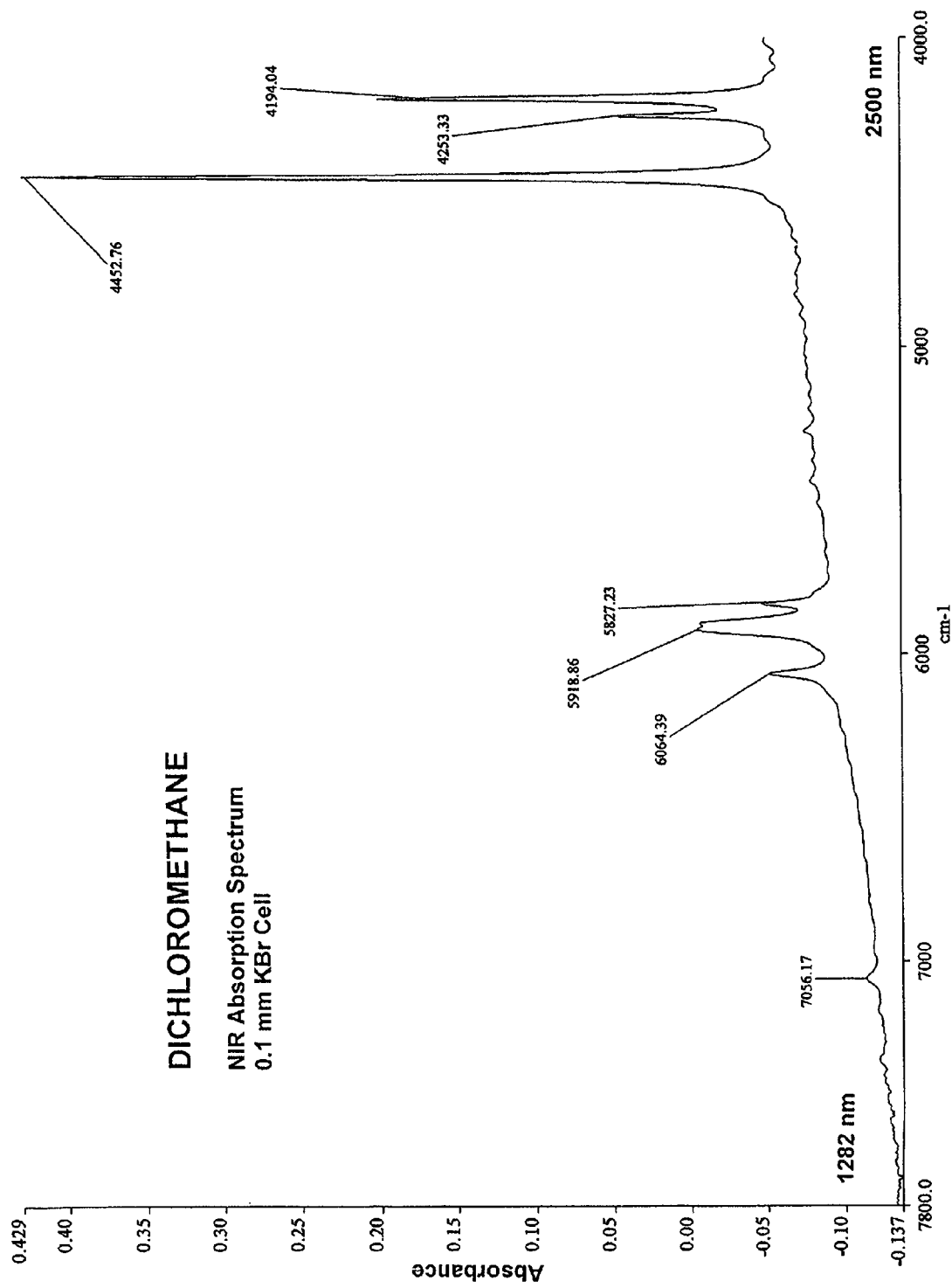
FIG. 9 shows a dichloromethane NIR absorption spectrum in accordance with some embodiments of the present invention.

As discussed above, embodiments of the present invention may include emitting at least two wavelengths (101) onto a target (103) as can be understood from FIG. 2. This may include emitting at least two wavelengths onto a single target location (102) of a target. Embodiments may include simultaneously emitting at least two wavelengths onto a target or perhaps even alternatively emitting at least two wavelengths onto a target. As such, wavelengths may be sent at the same time or at different times perhaps onto the same target location. Embodiments may include emitting adjacent wavelengths onto a target. A target (103) may include air, vapors, a surface, dust, smoke, airborne particles, liquids, solids, containers, solid surfaces, cloth, bottles, water bottles, or the like.

Further, wavelength(s) may be emitted from a single radiation emitter or perhaps, in other embodiments, wavelengths may be emitted from multiple emitters, perhaps at least two radiation emitters. A single radiation emitter may emit a single wavelength. In embodiments, a single radiation emitter may emit different wavelengths perhaps even alternating between wavelengths. When using at least two radiation emitters, each radiation emitter may emit a different wavelength onto a target. Wavelengths may be selected from a near infrared spectrum, infrared spectrum, or other spectrum. In embodiments, a near infrared spectrum wavelength may include, but is not limited to a wavelength between about 1300 nm and about 2500 nm.

It appears possible that by illuminating vapors from explosive chemicals containing nitro groups with both laser wavelengths in air, liquids, or on a solid surface, the presence of such chemicals could be detected. For example, a simple ratio of scattered of reflected light for two adjacent wavelengths, one in which absorption occurs and one with little absorption from a focused detector could possibly serve as a remote indicator of IEDs.

Other embodiments of the present invention may include the use of a second harmonic wavelength to perform Near-Infrared (NIR) or Infrared (IR) detection of IEDs based on absorption by the presence of the nitro ($-NO_2$) functional group in explosives. The second harmonic of a nitro group infrared absorption may occur from about 3300 nm to about 3100 nm in the infrared. However, the strong C—H absorption from hydrocarbons or fuels (about 2900 $cm^{-1}$ to about 3100 $cm^{-1}$ or about 3440 nm to about 3226 nm) could cause interference in this region.

Solid state lasers are available for wavelengths of 2100 nm (holmium:YAG) and 2060 nm (holmium:YLF). Other lasers could be used also such as erbium:glass at 1540 nm, as a reference. Solid state diode lasers may be available for wavelengths of about 1,600 nm to about 3,800 nm from a Russian company, Independent Business Scientific Group. Photodiode detectors for the corresponding wavelengths may be used also. The wavelength of an individual laser can be changed by altering input current or diode temperature. Thus, it might be possible to use a single laser to toggle between both the sample and reference wavelength beams, while illuminating a single spot portion of suspect sample. This could eliminate any differences in signal due to variations in spatial beam alignment. It may be possible that by illuminating surfaces, vapors, or dust from explosive chemicals containing nitro groups with laser wavelengths in air or perhaps even on a solid surface, the presence of such chemicals may be detected.

Embodiments of the present invention may include a stand-off means perhaps including a displacement of molecules, dust, small soil particles or the like from a target having adsorbed explosive molecules from the IEDs into the air so that they may be detected, perhaps even remotely detected, in the air by a laser, for example by using the DIAL laser technique. To accomplish this, one may direct bursts of air, low frequency sound, focused or even unfocussed low frequency sound, or the like near a target. This may be analogous to the subwoofers used in some audio systems, often in automobiles, that may cause walls to rattle and dust to rise due to the boom-boom sound. Alternatively, the sound frequency may be sub-audible, which may cause a bump or even shaking of the target area without detection by the human ear. This may be accomplished perhaps with an air gun, or the like, to provide a directed puff of air. Air puffer devices provided by Smiths Detection or General Electric currently are used for airport screening in enclosed chambers.

Both laser beams and sound bursts may be aimed and focused on single spots from a stationary source, a moving platform such as a Humvee, armored vehicle, or airframe mounted platform, and the like. The beams may be scanned over 3-dimensional space to remotely profile a target area around the platform, to pinpoint the location of IEDs (or suicide bombers, as but one example). As such, embodiments of the present invention may include profiling a target in a 2-dimension or even 3-dimension fashion. It may be possible to detonate IEDs using the lasers once they have been located, by increasing the intensity of the laser source, using a third high-intensity laser, or even a projectile, and the like. Alternatively, a separate aimed laser or other device might be used to detonate the explosive. It also should be possible to develop an imaging sensor system by conducting an X/Y scan of a potential target area.

The concentration of nitro groups as discussed above in an explosives package may be relatively small. Explosive chemicals are relatively non-volatile and are considered to be "sticky", that is, they may be adsorbed onto solid surfaces (NRC 2004). It is on solid surfaces where they could be detected by this technique. Therefore, additional aspects may be explored for making the DIAL detector system as sensitive as possible. This may involve maximizing the signal-to noise ratio. Continuous, or even pulsed-mode with boxcar integration may be used in embodiments. Other embodiments may include a ratio of or difference between intensities of the two lasers beams, e.g., a ratio between at least two reflected near infrared wavelengths. First or second differentials could be used also.

Further embodiments may involve a laser that may simultaneously emit both wavelengths, which may automatically compensate for internal intensity fluctuations, and eliminate possible spatial differences in the target spot. A detector may be designed to maximize signal to noise as it detects the intensity of both wavelengths. One advantage of using infrared or perhaps even near infrared light may be that scattering may not be as significant as compared with blue and visible light. In embodiments, optics such as but not limited to silica based optics, quartz, glass, Corex glass, and the like may be used with near infrared. At about 3300 nm, salt based optics such as, but not limited to: silver, potassium, or sodium chlorides or bromides, and the like could be used. A detector may include a Light Detection and Ranging (LIDAR), Differential Absorption Lidar (DIAL), a photodiode, a photomultiplier, a photoconductive detector, a variety of other devices, depending on the wavelength, either single detector or array, or the like. Optimal signal and reference wavelengths may need to be selected to minimize possible interferences from infrared absorbing C—H and C—C bonds in fuel molecules, and C═O functional groups.

Figure 11:
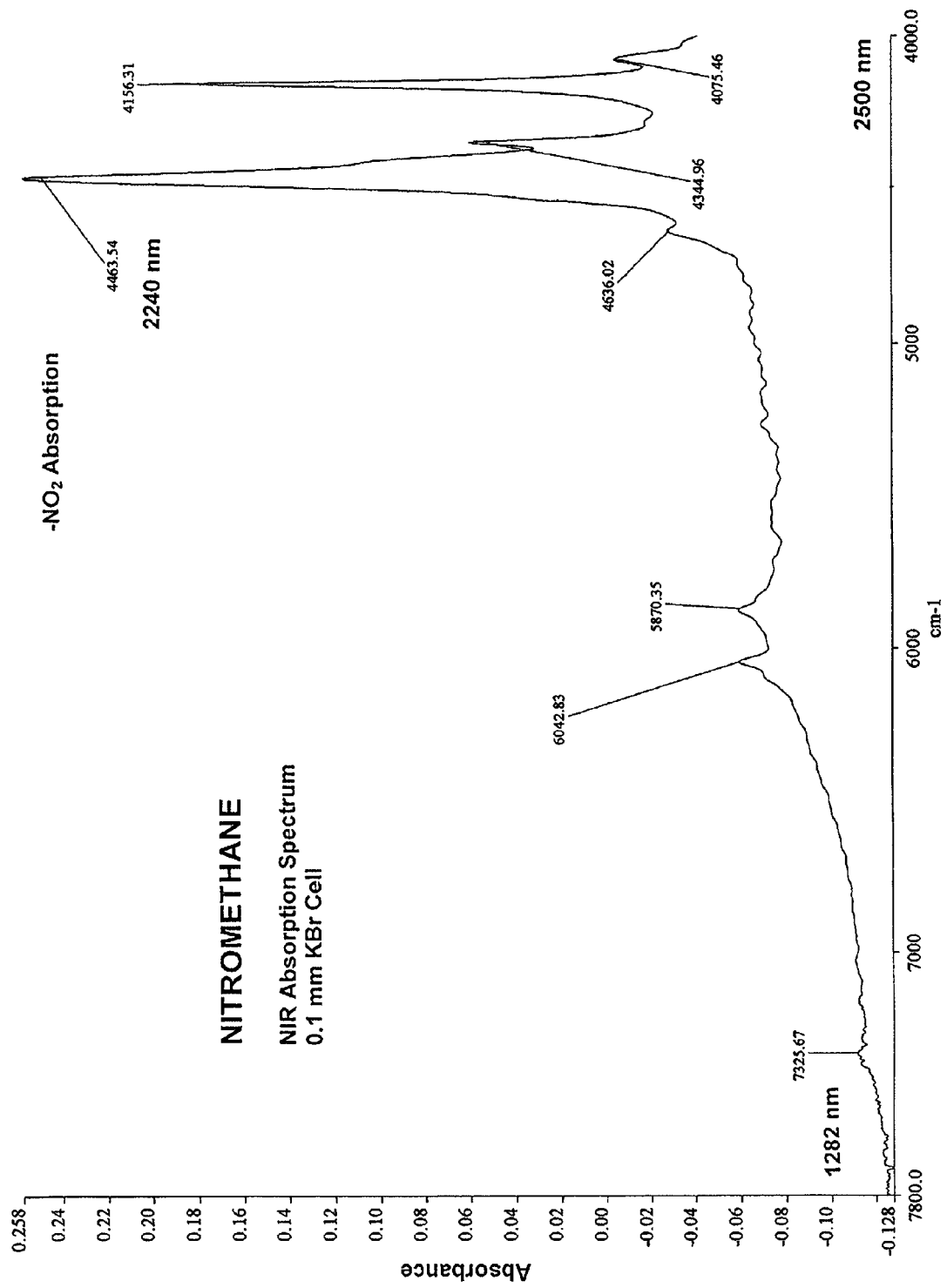
FIG. 11 shows a nitromethane NIR absorption spectrum in accordance with some embodiments of the present invention.
Figure 12:
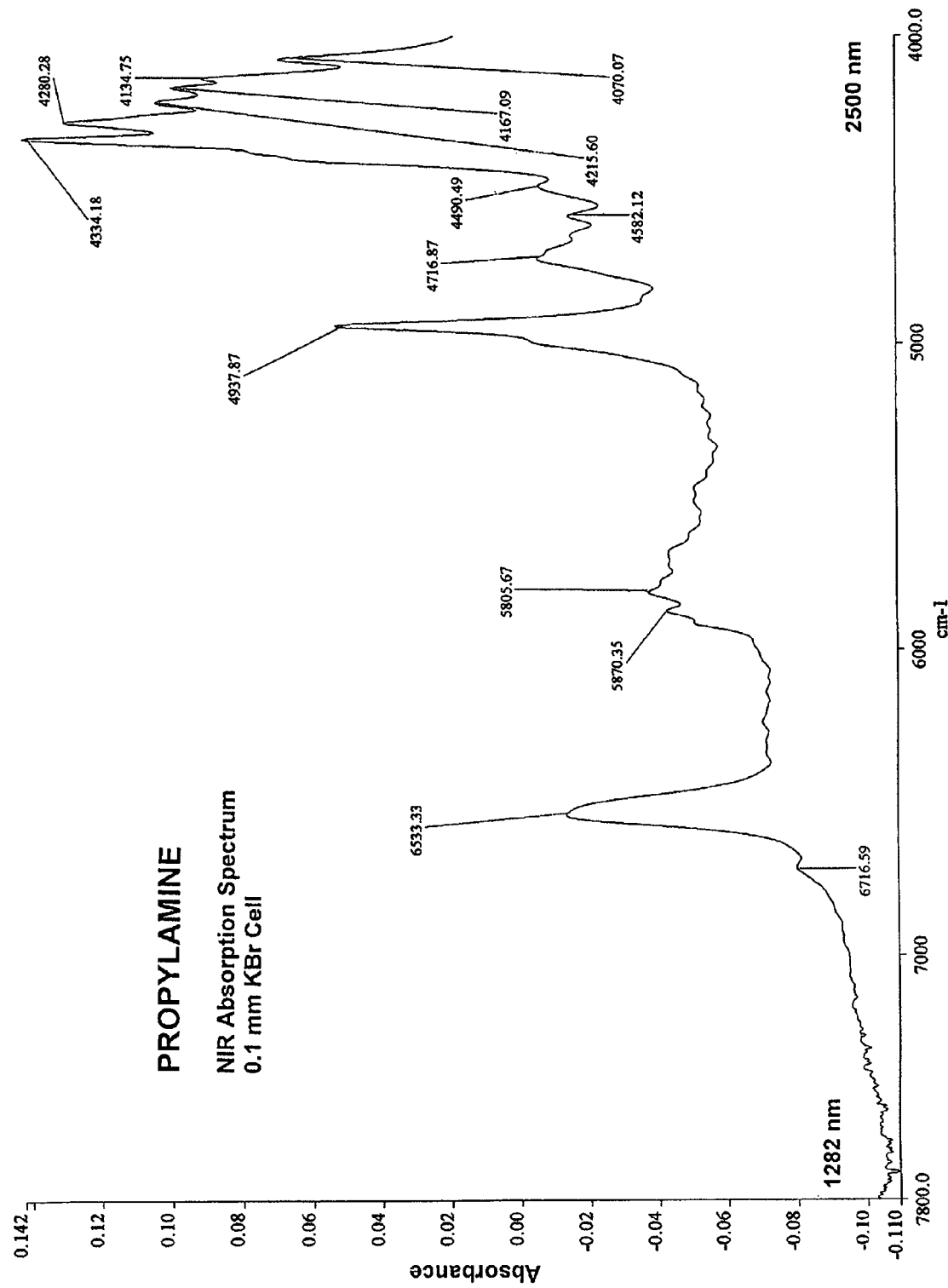
FIG. 12 shows a propylamine NIR absorption spectrum in accordance with some embodiments of the present invention.
Figure 13:
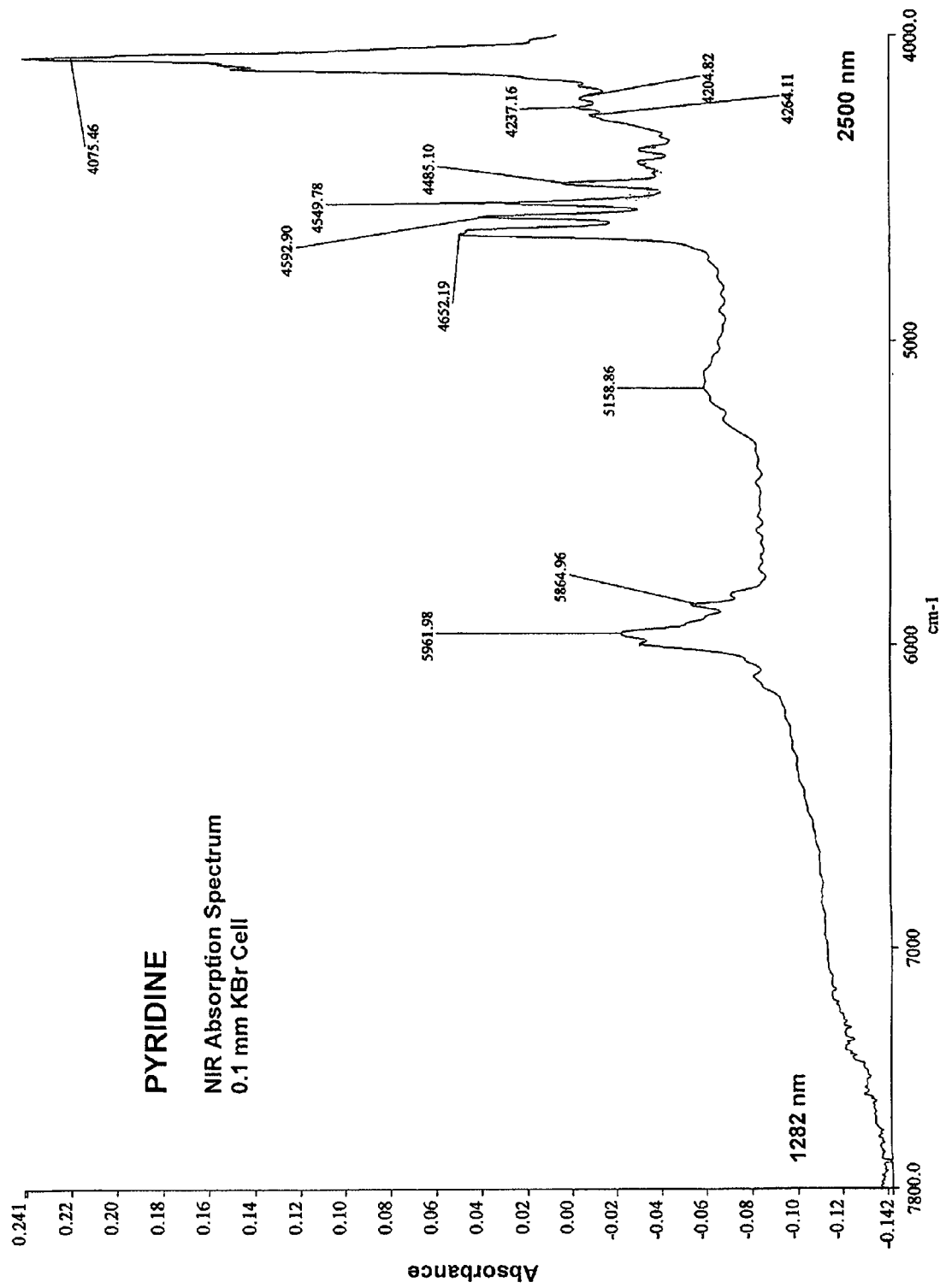
FIG. 13 shows a pyridine NIR absorption spectrum in accordance with some embodiments of the present invention.
Figure 14:
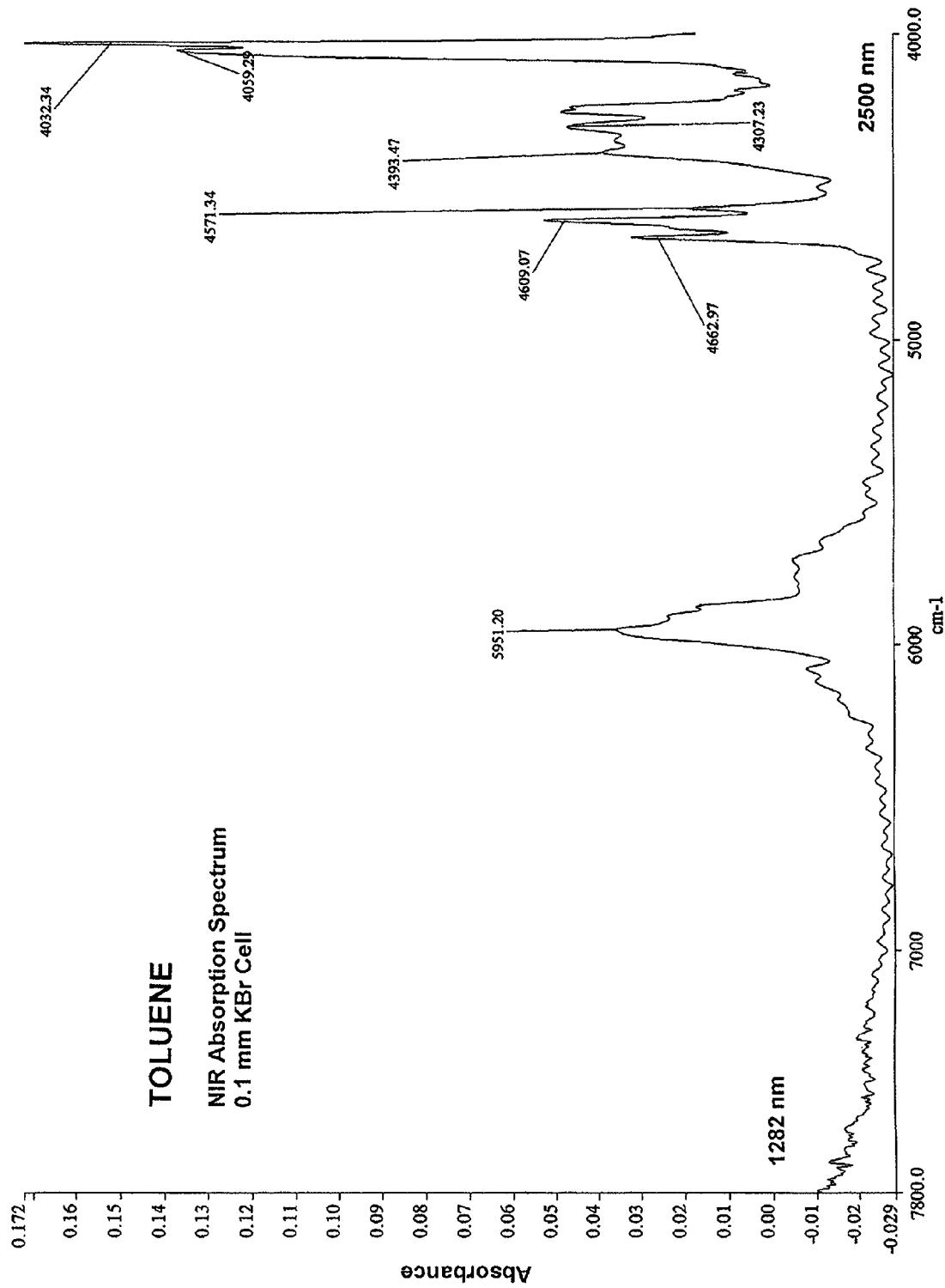
FIG. 14 shows a toluene NIR absorption spectrum in accordance with some embodiments of the present invention.
Figure 15:
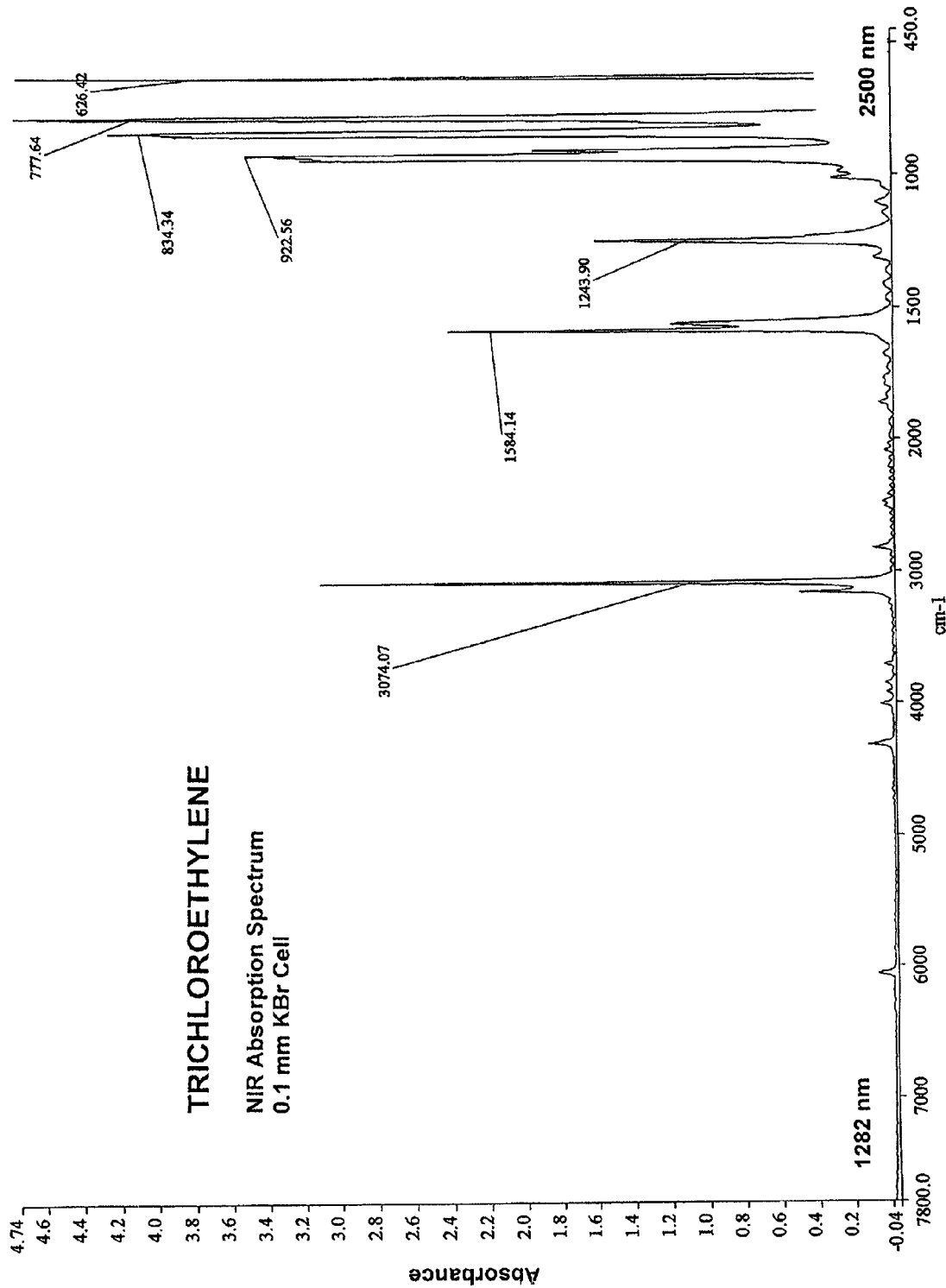
FIG. 15 shows a trichloroethylene NIR absorption spectrum in accordance with some embodiments of the present invention.
Figure 16:
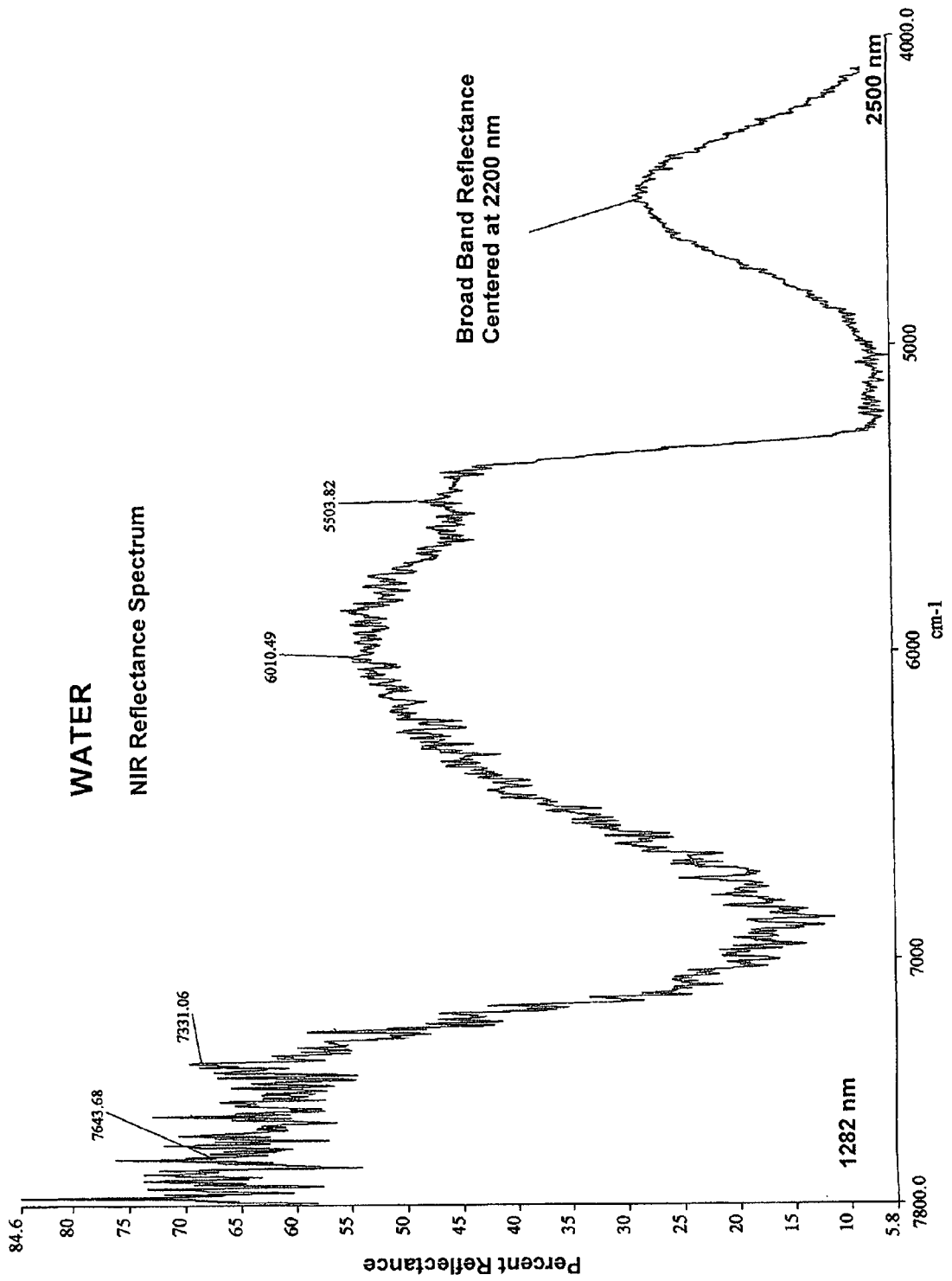
FIG. 16 shows a water NIR reflectance spectrum in accordance with some embodiments of the present invention.

As an example, using an IR/NIR instrument (e.g., a Perkin-Elmer Spectrum One laboratory IR/NIR FTIR instrument), NIR spectra for surrogate nitro compounds such as nitroethane (aliphatic) and nitrobenzene (aromatic), and a variety of organic solvents with different functional groups and water were obtained, see FIGS. 3-16. The solvent spectra were obtained with a KBr cell and 0.1 mm path length. The water spectrum was obtained by reflectance. Hydrocarbon solvents were included to mimic the response of fuel materials such as gasoline, jet fuel, diesel fuel, and other common solvents. This was done to study optimal wavelength regions for detection of nitro functional groups. Further, NIR spectra for two surrogate aliphatic nitro compounds, nitroethane and nitromethane were obtained, see FIGS. 10 and 11.

Embodiments of the present invention may provide analyzing the intensity of at least one reflected near infrared wavelength. An analyzer may include a computer system, software, hardware, or the like to analyze the reflected wavelengths or even the spectrum of the reflected wavelengths. In embodiments, an analyzer may analyze the difference between at least two wavelength intensities. An analyzer may detect an absorption of a reflected wavelength between about 1300 nm to about 2500 nm (about 8000 $cm^{-1}$ to about 4000 $cm^{-1}$), or between about 2000 nm to about 2500 nm (about 5000 $cm^{-1}$ to about 4000 $cm^{-1}$) or the like. These ranges may be indicative of explosive compounds containing nitro and/or carbonyl groups. In some embodiments, detection of a third harmonic vibrational absorption of a nitro or even carbonyl group may indicate an explosive device. Spectra may indicate significant signals in the NIR region for the nitro group harmonic absorption at, such as but not limited to, about 4200 $cm^{-1}$ to about 4500 $cm^{-1}$ (about 2381 nm to about 2222 nm). The spectra may show that the apparent complex third harmonic of the nitro group absorbance for nitromethane may be about 2240 nm and about 2250 nm for nitroethane. Corresponding third harmonic absorbance due to the carbonyl groups for some common chemicals may occur at slightly higher wavelengths for example: acetone at about 2265 nm, ethyl acetate at about 2259 nm, and glacial acetic acid at about 2259 nm. Although carbonyl groups may show similar absorption characteristics in the region, their peak may occur at slightly higher wavelengths. In IR spectroscopy, a strong carbonyl peak may be near about 1600 $cm^{-1}$, while a strong nitro peak may typically be at a lower frequency, such as about 1550 $cm^{-1}$. The exact frequency may depend on the particular compound, its structural environment, and if it is a liquid, solid, vapor, or adsorbed to a surface.

In embodiments, the present invention may include differentiating between a nitro group and a carbonyl group. A carbonyl compound may be differentiated from a nitro compound by selecting an off-peak or perhaps even shoulder wavelength for the nitro groups where the nitro groups may exhibit some absorbance, and where the carbonyl group does not generally absorb, such as but not limited to about 4500 cm−1 (about 2222 nm). NIR spectra for other chemicals such as carbon disulfide, heptane, methanol, methylene chloride, propylamine, pyridine, toluene, trichloroethylene, or water show that these should not cause significant interferences. We certainly do not want a jar of pickles to provide a signal that is mistaken for an explosive nitro containing material. However, acetic acid or acetone may not be expected to be found in a water bottle taken through airport security. In embodiments, it may be desirable to take into account the spectral signature of the containers themselves. Members of a particular class of non-nitro containing explosive, diacetone and triacetone peroxides (i.e. TATP), could be detected with a selectively tuned version of this device since they contain carbonyl groups. Water may have a broad based low absorption in the region, which may not be a problem if a nearby wavelength may be used for a reference signal.

With appropriate signal processing, it could be possible to differentiate the nitro group absorbance from carbonyl group absorbance, so that a jar of pickles, for example, will not set off an alarm. Optimal wavelength regimen or procedures to detect nitro or carbonyl functional groups could be determined with reference spectra of actual explosives materials perhaps even explosives adsorbed onto solid surfaces such as cloth, metal, or the like. For example, reflectance spectra of explosives material adsorbed onto solid surfaces might have spectral signatures at slightly different wavelengths than nitroethane or nitromethane.

A positive signal, for example, could be interpreted when comparing a ratio of two reflected wavelengths to a predetermined value. For example, a ratio of reflected signal from a nearby reference signal may exceed a reflectance signal of the analytical wavelength, for example when calculating about 4630 $cm^{-1}$ about 4500 $cm^{-1}$ (or about 2222 nm/about 2160 nm) or even about 4600 $cm^{-1}$/about 4500 $cm^{-1}$ (or about 2222 nm/about 2174 nm) signal ratio may be greater than one, or perhaps 1.3 or some other predetermined value. NIR spectra of pure chemicals may show that only the nitro compounds exhibit such a ratio. This could be used to easily distinguish the nitro compounds from the carbonyl compounds. For standoff IED detection, both signals could be from the same physical spot on the sample for a reflectance mode. In embodiments, such as for airport water bottle screening, an enclosed device with a moving belt could be employed at transmittance mode of operation. For airport screening, we also would have to take into account the spectral signature of the containers themselves. Members of a particular class of non-nitro containing explosive, diacetone and triacetone peroxides (i.e. TATP), could be detected with a selectively tuned version of this device since they contain carbonyl groups.

Other embodiments of the present invention may include optimizing detection limits. For screening liquids in clear containers such as water bottles and the like at an airport screening station, this may not be an issue; however, screening for traces of explosives on clothing (perhaps clothing of a homicide bomber) backpacks, packages, and the like, may present a detection limit challenge. To optimize the detection limit, it may be desirable to use tunable diode lasers to be able to rapidly switch between analytical and reference wavelengths using the same laser, thereby eliminating signal intensity differences that would otherwise occur when more than one laser is used.

As can be easily understood from the foregoing, the basic concepts of the present invention may be embodied in a variety of ways. It involves both detection techniques as well as devices to accomplish the appropriate detector. In this application, the detection techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s)

shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "detector" should be understood to encompass disclosure of the act of "detecting"—whether explicitly discussed or not—and, conversely, were there effectively disclosure of the act of "detecting", such a disclosure should be understood to encompass disclosure of a "detector" and even a "means for detecting." Such changes and alternative terms are to be understood to be explicitly included in the description.

Any patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in any Information Disclosure Statements or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the detection devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, xii) each potentially dependent claim or concept as a dependency on each and every one of the independent claims or concepts presented, and xiii) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A method of detecting explosives comprising the steps of:
   directing at least one laser onto a single spot of a target;
   emitting a single near infrared absorption wavelength from said at least one laser towards said single spot of said target, wherein said single near infrared absorption wavelength consists of a single near infrared wavelength capable of absorption by a chemical group selected from a group consisting of a nitro group and a carbonyl group on said single spot of said target;
   emitting a single reference wavelength from said at least one laser towards said single spot of said target, wherein said single reference wavelength consists of a single wavelength that is different from said single near infrared absorption wavelength;
   colliding said single near infrared absorption wavelength and said single reference wavelength with said target at said single spot of said target;
   generating a reflected wavelength from both said single near infrared absorption wavelength and said single reference wavelength after said collision of said single near infrared absorption wavelength and said single reference wavelength with said target at said single spot of said target;
   detecting an intensity of each of said reflected wavelengths;
   analyzing said intensity of each of said reflected wavelengths; and
   determining if said target has an explosive compound when said target has molecules of a chemical group selected from a group consisting of a nitro group and a carbonyl group based on said step of analyzing said intensity of each of said reflected wavelengths.

2. A method of detecting explosives according to claim 1 wherein said step of directing at least one laser onto a target comprises the step of selecting a step from a group consisting of:
   directing a single laser onto said single spot of said target; and
   directing two lasers onto said single spot of said target.

3. A method of detecting explosives according to claim 1 wherein said single reference wavelength is capable of absorption by said single spot of said target to a lesser extent than said single near infrared absorption wavelength.

4. A method of detecting explosives according to claim 1 wherein said laser is selected from a group consisting of a near infrared laser, a solid state laser, a solid state diode laser, a continuous mode laser, a pulsed mode laser, a boxcar integrated laser, and a tunable diode laser.

5. A method of detecting explosives according to claim 1 wherein said step of directing said at least one laser onto said single spot of said target comprises the step of directing at least one laser from a moving platform onto said single spot of said target.

6. A method of detecting explosives according to claim 1 wherein said step of emitting said single near infrared absorption wavelength and said single reference wavelength onto said single spot of said target comprises the step of simultaneously emitting said single near infrared absorption wavelength and said single reference wavelength onto said single spot of said target.

7. A method of detecting explosives according to claim 1 wherein said step of emitting said single near infrared absorption wavelength and said single reference wavelength onto said single spot of said target comprises the step of alternatively emitting each of said single near infrared absorption wavelength and said single reference wavelength onto said single spot of said target.

8. A method of detecting explosives according to claim 1 wherein said single near infrared absorption wavelength is between about 1300 nm and about 2500 nm.

9. A method of detecting explosives according to claim 1 wherein said step of detecting an intensity of each of said reflected wavelengths comprises the step of detecting said intensity with a detector selected from a group consisting of Light Detection and Ranging (LIDAR), Differential Absorption Lidar (DIAL), a photodiode detector, a photomultiplier, and a photoconductor detector.

10. A method of detecting explosives according to claim 1 wherein said step of detecting an intensity of each of said reflected wavelengths comprises the step of detecting said intensity with a single detector.

11. A method of detecting explosives according to claim 1 wherein said step of detecting an intensity of each of said reflected wavelengths comprises the step of detecting said intensity with multiple detectors.

12. A method of detecting explosives devices according to claim 1 and further comprising the step of displacing molecules from a surface of said target.

13. A method of detecting explosives according to claim 12 wherein said step of displacing molecules from said surface of said target comprises molecule displacement selected from a group consisting of:
   directing a burst of low frequency sound near said target;
   directing a burst of focused low frequency sound near said target;
   directing a burst of unfocussed low frequency sound near said target; and
   directing a burst of air near said target.

14. A method of detecting explosives according to claim 1 and further comprising the step of utilizing optics selected from a group consisting of silica based optics, quartz, glass, and Corex glass.

15. A method of detecting explosives according to claim 1 wherein said target is selected from a group consisting of air, vapors, a surface, dust, smoke, airborne particles, liquids, solids, containers, solid surfaces, cloth, bottles, and water bottles.

16. A method of detecting explosives according to claim 1 wherein said step of analyzing said intensity of each of said reflected wavelengths comprises the step of analyzing a difference between each of said reflected wavelength intensities.

17. A method of detecting explosives according to claim 1 wherein said step of analyzing said intensity of each of said reflected wavelengths comprises the steps of calculating a ratio between each of said reflected wavelengths and comparing said ratio to a predetermined value.

18. A method of detecting explosives according to claim 1 and further comprising the step of profiling said target in a dimension selected from a group consisting of 2-dimension (2-D) and 3-dimension (3-D).

19. A method of detecting explosives according to claim 1 wherein said step of determining if said target has molecules of a chemical group selected from a group consisting of a nitro group and a carbonyl group comprises the step of detecting an absorption in either of said reflected wavelengths, said absorption selected from a group consisting of:

between about 1300 nm to about 2500 nm (about 8000 $cm^{-1}$ to about 4000 $cm^{-1}$); and between about 2000 nm to about 2500 nm (about 5000 $cm^{-1}$ to about 4000 $cm^{-1}$).

20. A method of detecting explosives according to claim 1 wherein said step of determining if said target has an explosive compound when said target has molecules of a chemical group selected from a group consisting of a nitro group and a carbonyl group comprises the step of detecting third harmonic vibrational absorption of a nitro group or a carbonyl group in either of said reflected wavelengths.

21. A method of detecting explosives according to claim 1 wherein said single near infrared absorption wavelength and said single reference wavelength comprises two adjacent near infrared wavelengths.

22. A method of detecting explosives according to claim 1 wherein said steps of emitting said single near infrared absorption wavelength and said single reference wavelength from said at least one laser comprises the step of emitting said single near infrared absorption wavelength and said single reference wavelength from a single laser.

23. A method of detecting explosives according to claim 1 wherein said steps of emitting said single near infrared absorption wavelength and said single reference wavelength from said at least one laser comprises the step of emitting said single near infrared absorption wavelength and said single reference wavelength from two lasers.

24. A method of detecting explosives according to claim 1 and further comprising the step of differentiating said nitro group from said carbonyl group.

25. An explosive detection apparatus comprising:

at least one laser;

a single near infrared absorption wavelength generated from said at least one laser, wherein said single near infrared absorption wavelength consists of a single near infrared wavelength capable of absorption by a chemical group selected from a group consisting of a nitro group and a carbonyl group on a target;

a single reference wavelength generated from said at least one laser, wherein said single reference wavelength consists of a single wavelength that is different from said single near infrared absorption wavelength;

a reflected wavelength detector of a reflected single near infrared absorption wavelength and a reflected single reference wavelength generated after said single near infrared absorption wavelength and said single reference wavelength collides with a single spot of said target; and a reflected wavelength analyzer to determine if said target has an explosive element when molecules of a chemical group selected from a group consisting of a nitro group and a carbonyl group.

* * * * *